(12) United States Patent
Miledi

(10) Patent No.: US 9,272,117 B2
(45) Date of Patent: Mar. 1, 2016

(54) INTRA-NASAL AROMATHERAPY CLIP

(71) Applicant: Gary Miledi, Irving, TX (US)

(72) Inventor: Gary Miledi, Irving, TX (US)

(73) Assignee: Gary Miledi, Irving, TX (US)

( * ) Notice: Subject to any disclaimer, the term of this patent is extended or adjusted under 35 U.S.C. 154(b) by 528 days.

(21) Appl. No.: 13/689,678

(22) Filed: Nov. 29, 2012

(65) Prior Publication Data

US 2013/0150658 A1    Jun. 13, 2013

Related U.S. Application Data

(60) Provisional application No. 61/567,807, filed on Dec. 7, 2011.

(51) Int. Cl.
*A61M 15/08*     (2006.01)
*A61M 21/02*     (2006.01)
*A62B 9/06*      (2006.01)
*A61M 21/00*     (2006.01)

(52) U.S. Cl.
CPC ............. *A61M 21/02* (2013.01); *A61M 15/08* (2013.01); *A61M 15/085* (2014.02); *A61M 2021/0016* (2013.01); *A62B 9/06* (2013.01)

(58) Field of Classification Search
CPC .......... A61M 16/0666–16/0677; A61M 15/08; A61M 15/085; A62B 23/06; A61F 5/08
See application file for complete search history.

(56) References Cited

U.S. PATENT DOCUMENTS

| | | | |
|---|---|---|---|
| 2,672,138 A | 3/1954 | Oarlock | |
| 3,747,597 A * | 7/1973 | Olivera | 128/206.11 |
| 4,984,302 A * | 1/1991 | Lincoln | 2/206 |
| 6,701,924 B1 * | 3/2004 | Land et al. | 128/206.11 |
| 7,156,099 B1 | 1/2007 | Jenkins | |
| 2006/0150980 A1 * | 7/2006 | Kim | 128/206.18 |
| 2007/0062538 A1 * | 3/2007 | Foggia et al. | 128/207.18 |
| 2008/0092889 A1 * | 4/2008 | Tjia | 128/204.13 |
| 2010/0147300 A1 * | 6/2010 | Lorenzati et al. | 128/204.14 |
| 2014/0246023 A1 * | 9/2014 | Maryanka | 128/203.22 |

* cited by examiner

*Primary Examiner* — Valerie L Skorupa

(57) ABSTRACT

Described is an intra-nasal clip, and more particularly a nasal clip that diffuses the aromas or fragrances, such as those used in aromatherapy, of an aromatherapy sphere without irritation through direct contact with the inner nasal septum. The intra-nasal clip includes a bendable bridge extending between its outer distal ends, in which the distal ends comprise hollows with inlets. Aromatherapy spheres are within the hollows that contain aromatherapy materials.

6 Claims, 9 Drawing Sheets

INTRA-NASAL AROMATHERAPY CLIP

FIELD OF THE INVENTION

The present invention relates generally to the field of intra-nasal clips, and more particularly to a nasal clip that effuses aromas or fragrances, such as those used in aromatherapy, as well as for dispensing through the nasal passage aromatically ingestible medicines.

BACKGROUND INFORMATION

Various aromas/medications give relief in various forms including nausea in people such as pregnant women with morning sickness, people undergoing chemotherapy, people with motion sickness, and people with other various ailments that may cause dizziness or queasiness. Aromatherapy is the practice of using aromatic substances for the treatment of illnesses or to enhance the health and well-being of the patient. Aromatherapy may use essential oils such as those from volatile plant oils or pure essence of a plant that is generally broken down and distilled from various parts of a plant. It can also use other aromatic materials that enhance patient's quality of life that can have an energizing effect.

Aromatherapy is practical as it can enhance a patient's quality of life by easing certain symptoms such as nausea deriving from various ailments. This happens because the aroma of certain oils or substances may stimulate the brain to trigger a reaction. Inhalation is the principal method of administration, but doing so usually requires extra-nasal administration. For example, using a handkerchief that is dabbed in essential oils may allow for inhalation of the aromatic substance, but may be impractical for those substances, especially of the concentrated kind, that are irritable to the skin. There are many other methods for utilizing the aromatic substances for aromatherapy, but many of them such as steamers, candles, clay pots, etc are all products that diffuse the scent of the oil outside the nose and affect everyone in the area that would smell the product.

There are nasal clips that are used in aromatherapy, but many of them are extra-nasal clips that diffuse the oil outside the nose and emit fragrances from outside the nostril. However, in these extra-nasal clips, the clips may lose most of the aromas to the air outside of the nose, where the aromas are emitted, and not directly into the nostrils. This would make the extra-nasal clips to not have as potent an effect on the patient as an intra-nasal clip. Nasal administrations of medicines by direct contact from squirting or pumping medicine may irritate nasal tissue of the user. Clips that hold open the nasal septum would not be desirable in this context as user would want the administration of the aromatherapy to not be lost outside of the nasal septum.

Therefore, there is a need to provide an intra-nasal clip, which diffuses aromatherapy efficiently into the nasal septum of the user without risk of being an irritant to the inner nasal septum by exposing the user to irritating contact of the aromatherapy material.

SUMMARY

The invention is directed to an aromatherapy dispensing intra-nasal clip which includes a bendable bridge extending between its outer distal ends, in which the distal ends comprise hollows with inlets. Within the hollows are aromatherapy spheres that contain either the essential oils or other aromatherapy materials that allow the oils to aerate through the inlets of the hollows without having to have liquid materials within the nose or risk irritation from direct contact of the aromatherapy materials with the inner nasal septum. The concentration of each type of aromatic substance will determine the length of time the aromatherapy spheres will be soaked.

An embodiment of the invention comprises an intra-nasal clip comprising a bridge, a distal end, a second distal end, an aromatherapy sphere for both the distal end and the second distal end, and a plurality of inlets located on both the distal end and the second distal end. The distal end further comprises a hollow which may be filled with the aromatherapy sphere in addition to essential oils, aromatherapy liquids or other substances. The plurality of inlets located on both the distal end and the second distal end further comprises a cross-shaped inlet. The plurality of inlets located on both the distal end and the second distal end further comprises a row of inlets. The distal end further comprises a distal bowl that holds the aromatherapy sphere, an end-lid, and a snap that connects to the end-lid that is moveable which allows for replacement of the aromatherapy sphere. The second distal end further comprises a distal bowl that holds the aromatherapy sphere, an end-lid, and a snap that connects to the end-lid that is moveable which allows for replacement of the aromatherapy sphere. The snap that connects to the end-lid that is moveable which allows for replacement of the aromatherapy sphere further comprises a snap that locks into an edge of the end-lids. The snap that connects to the end-lid that is moveable which allows for replacement of the aromatherapy sphere further comprises a snap that locks into an edge of the end-lids.

Another embodiment of the invention comprises a method of administering aromatherapy. The method of administering aromatherapy comprises choosing an essential oil, aromatherapy liquid or other substance, installing an aromatherapy sphere inside a distal end of an intra-nasal clip; and inserting the intra-nasal clip inside a user's nose.

The inner surface of the bridge contacts the respective right and left sides of a user's nasal septum when the distal ends are inserted in the user's right and left nostrils. The bridge and distal ends are preferably molded of a resin such as polyvinyl chloride, polycarbonate, or a number of other non-irritating plastic resins with suitable use in flexibility and compatibility with the aromatherapy material being used. The aromatherapy spheres within the distal ends are preferably made of rubber, wood, or a number of plastic resins that are appropriate in compatibility of the aromatherapy being used. The preferred embodiment uses a bridge having a geometry that utilizes pressure at its attachment points within the user's nasal septum. This geometry allows the bridge to fit over the bulbous end of the nasal septum while staying in place without obstructing the air passageway of the nose.

BRIEF DESCRIPTION OF THE DRAWINGS

The present invention and other attributes of the invention can best be understood in connection with the accompanying drawing in which.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing the spirit or scope of the invention. To avoid detail not necessary to enable those skilled in the art to practice the embodiments, the description may omit certain information known to those skilled in the art. The following detailed description is, therefore, not to be taken in a limiting sense.

Figure 1:
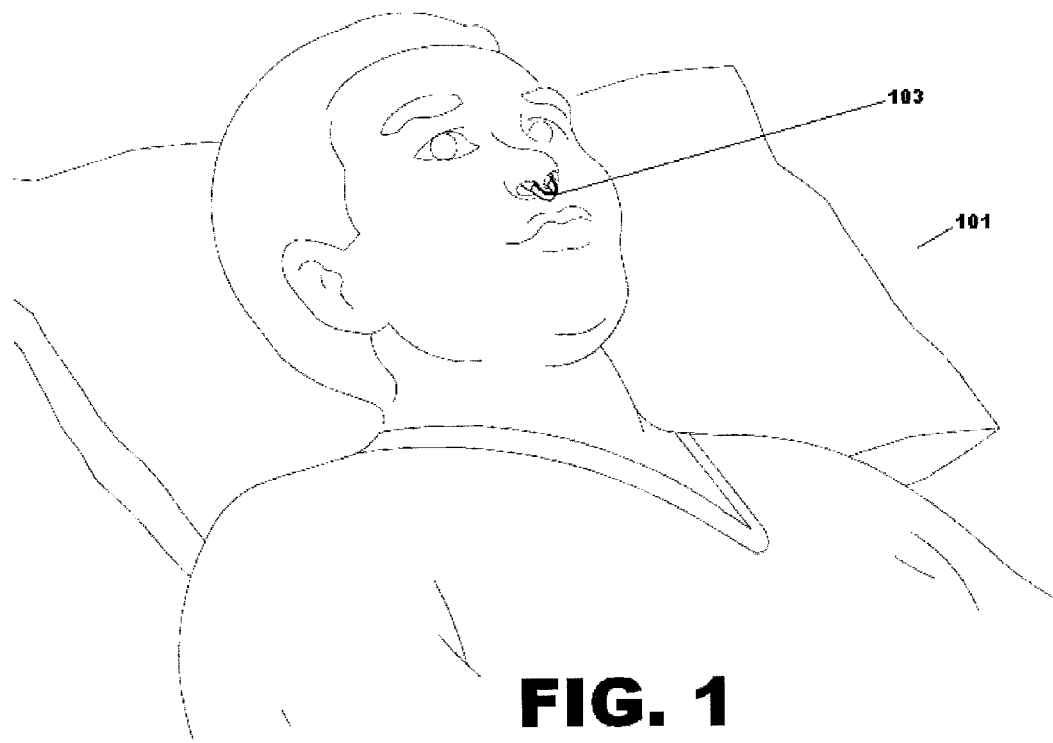
FIG. 1 is a side view of a facial profile of a user with the present invention in use.

Referring now to FIG. 1, user 101 will wear intra-nasal clip 103 for aromatherapy use or for uses that involve administering medicine nasally. Intra-nasal clip 103 is preferably molded of a resin such as polyvinyl chloride, polycarbonate, or a number of other non-irritating plastic resins with suitable use in flexibility and compatibility with the aromatherapy material being used. When worn, the intra-nasal clip is hardly visible and fits comfortably within user 101 even while lying down as shown in FIG. 1.

Figure 2:
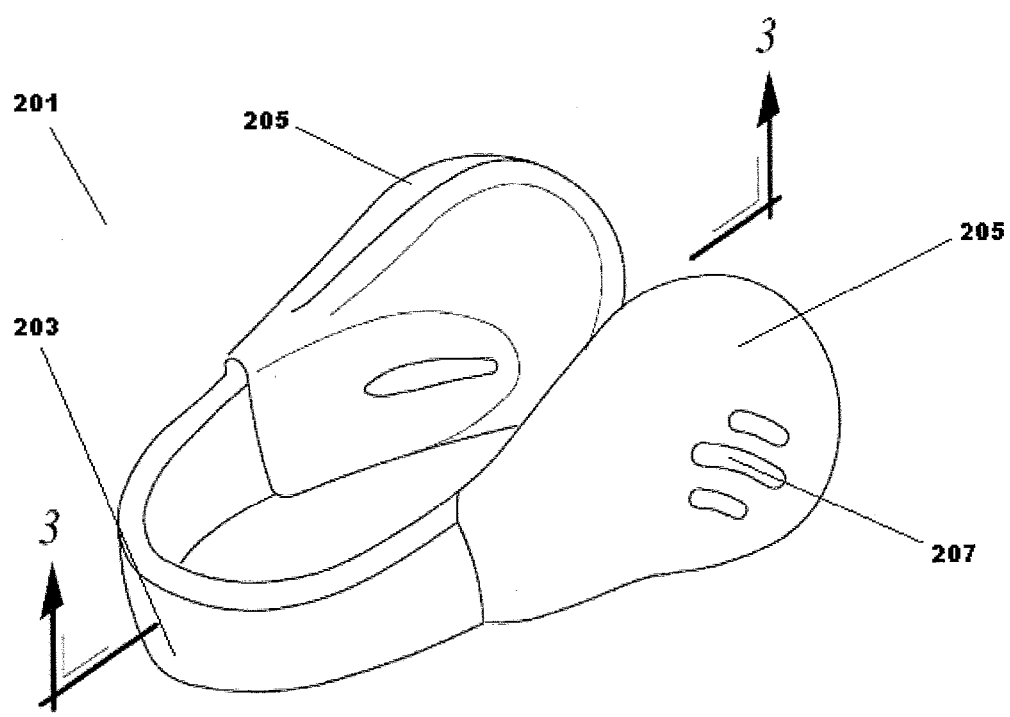
FIG. 2 is a perspective view of a preferred embodiment of the current invention, intra-nasal dispenser clip.

Referring now to FIG. 2, intra-nasal clip 201 comprises bridge 203, distal ends 205, and inlets 207. Another requirement is to prevent contact of the aromatherapy material with the inner nasal septum to avoid irritation with the sensitive nasal mucous membranes. This is possible by connecting to bridge 203 with distal ends 205. The preferred embodiment uses bridge 203 having a geometry that utilizes pressure at its attachment points within the user's nasal septum. This geometry allows bridge 203 to fit over the bulbous end of the nasal septum while staying in place without obstructing the air passageway of the nose. Distal ends 205 further comprise inlets 207, which help to prevent spillage of aromatherapy materials inside the distal ends 205 to the outside. Distal ends 205 can take up a variety of geometries and shapes. Distal ends 205 are preferably molded of a resin such as polyvinyl chloride, polycarbonate, or a number of other non-irritating plastic resins with suitable use in flexibility and compatibility with the aromatherapy material being used. Inlets 207 may take a variety of geometries, of which in FIG. 2, we are shown slits that allow the aromatherapy vapors to escape from within distal ends 205. FIG. 2 shows a preferred embodiment of the intra-nasal aromatherapy clip by showing how the inlets on the sides of the distal ends allow the aromatherapy balls to diffuse the aroma or fragrance to the user without spillage of the aromatherapy material into the inner nasal septum.

Figure 3:
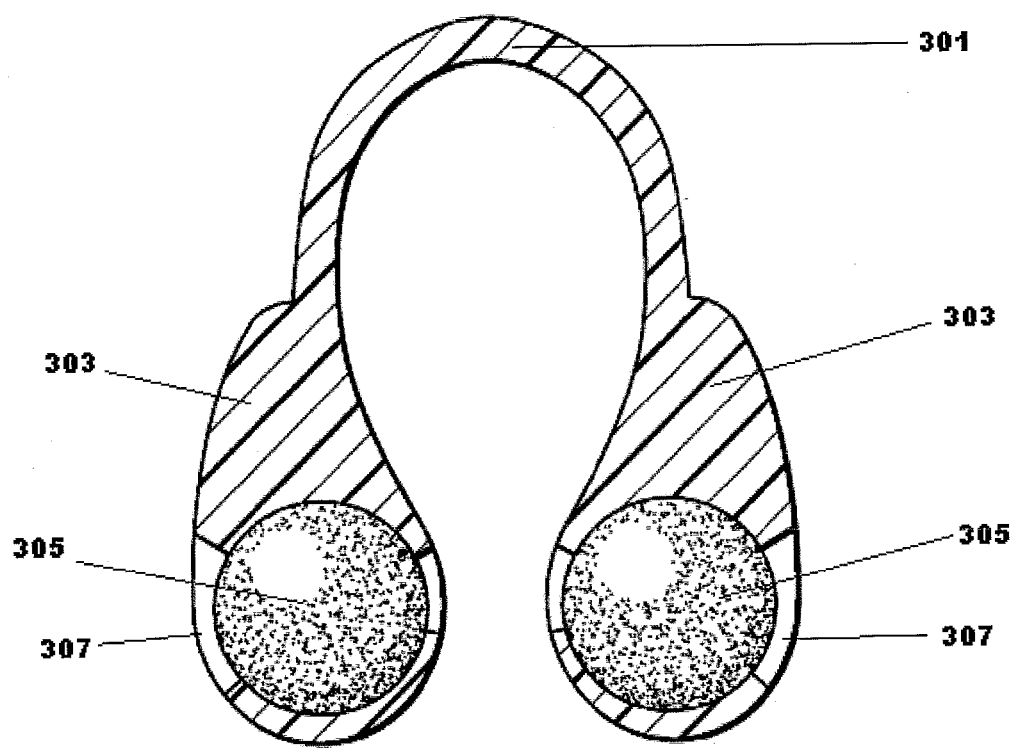
FIG. 3 is a front cross section detail showing the aromatherapy spheres inside the hollow distal ends orbs.

Referring now to FIG. 3, bridge 301 connects distal ends 303. Distal ends 303 further comprise inlets 307 and aromatherapy spheres 305. Distal ends 305 comprise inlets 307 which are on the outer side of distal ends 305 so that inlets 307 are facing outwards. Inlets 307 may take various geometries and shapes to allow for most effective aromatherapy use and may be adjusted to allow for various types of aromatherapies. Aromatherapy spheres 305 inside distal ends 303 of the intra-nasal clip may fit variably within distal ends 303 as may be appropriate for the aromatherapy as the aromatherapy spheres 305 may be comprised of material not limited to rubber, wood, and various other plastic resins. Aromatherapy spheres 305 within distal ends 303 are preferably made of rubber, wood, or a number of plastic resins that are appropriate in compatibility of the aromatherapy being used. FIG. 3 displays one preferred embodiment of how aromatherapy spheres 305 fit within the distal ends 303 of the intra-nasal clip. Aromatherapy spheres 305 that contain either the essential oils or other aromatherapy materials allow the oils to aerate through inlets 307 of distal ends 305 without having to have liquid materials within the nose or risk irritation from direct contact of the aromatherapy materials with the inner nasal septum. The concentration of each type of aromatic substance will determine the length of time the aromatherapy spheres will be soaked.

Figure 4:
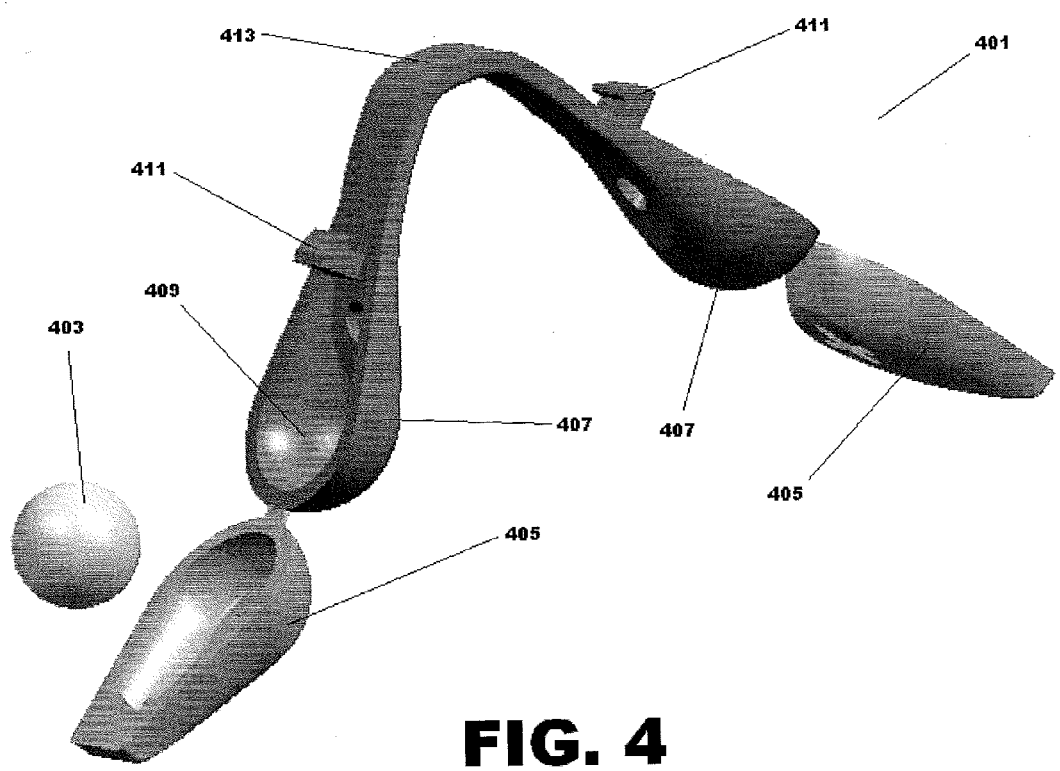
FIG. 4 is a perspective view of a preferred embodiment of the current invention, intra-nasal dispenser clip.

Referring now to FIG. 4, intra-nasal clip 401 comprises aromatherapy spheres 403, end-lids 405, distal ends 407, distal bowls 409, snaps 411, and bridge 413. FIG. 4 displays one preferred embodiment of how intra-nasal clip 401 is comprised so that aromatherapy spheres 403 can be replaced and be allowed to be mixed and matched by user. Aromatherapy spheres 403 are placed into distal bowls 409, where aromatherapy spheres 403 fits. In order to secure placement of aromatherapy spheres 403 in distal bowls 409, end-lids 405 must be closed towards distal ends 407. Once end-lids 405 are closed towards distal ends 407, snaps 411 will lock into end-lids 405 to secure aromatherapy spheres 403 inside distal bowls 409. Bridge 413 connects with snaps 411, distal bowls 409, and distal ends 407. This particular preferred embodiment uses bridge 413 having a geometry that utilizes pressure at its attachment points within the user's nasal septum. This geometry allows bridge 413 to fit over the bulbous end of the nasal septum while staying in place without obstructing the air passageway of the nose.

Figure 5:
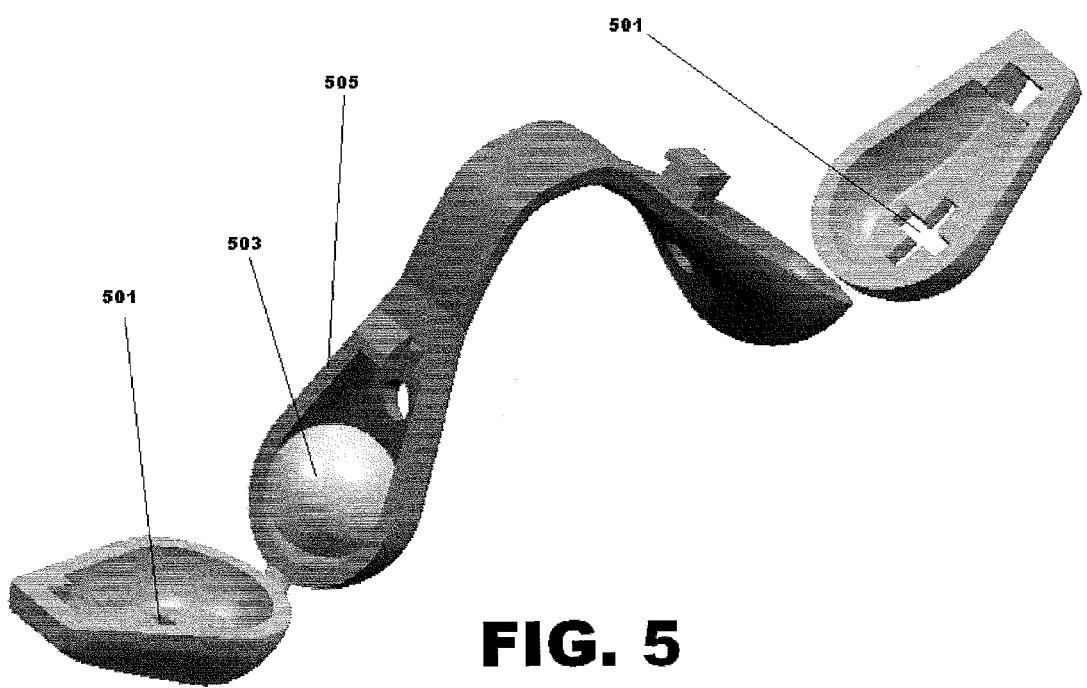
FIG. 5 is another perspective view of a preferred embodiment of the current invention, intra-nasal dispenser clip.

Referring now to FIG. 5, a perspective view of intra-nasal clip is shown, where inlets 501 is shown which once closed will secure aromatherapy spheres 503 inside distal ends 505. Inlets 501 may take a variety of geometries, of which in FIG. 5, we are shown a cross formation that allow the aromatherapy vapors to escape from within distal ends 505. Aromatherapy spheres 503 inside distal ends 505 of the intra-nasal clip may fit variably within distal ends 505 as may be appropriate for the aromatherapy as the aromatherapy spheres 503 may be comprised of material not limited to rubber, wood, and various other plastic resins. Aromatherapy spheres 503 within distal ends 505 are preferably made of rubber, wood, or a number of plastic resins that are appropriate in compatibility of the aromatherapy being used. FIG. 5 displays one preferred embodiment of how aromatherapy spheres 3503 fit within the distal ends 505 of the intra-nasal clip. Aromatherapy spheres 503 that contain either the essential oils or other aromatherapy materials allow the oils to aerate through inlets 501 of distal ends 505 without having to have liquid materials within the nose or risk irritation from direct contact of the aromatherapy materials with the inner nasal septum. The concentration of each type of aromatic substance will determine the length of time the aromatherapy spheres will be soaked.

Figure 6:
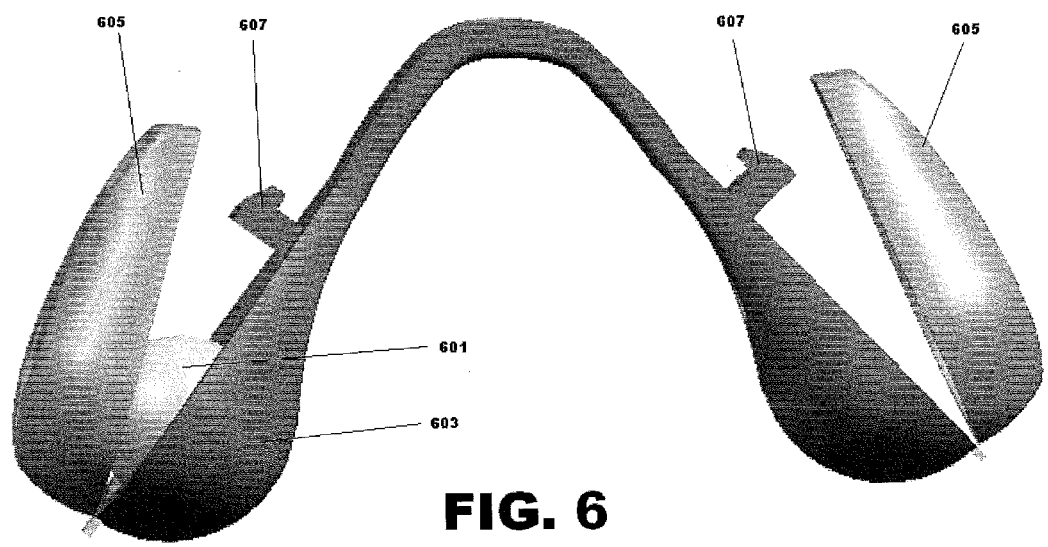
FIG. 6 is a side view of a preferred embodiment of the current invention, intra-nasal dispenser clip.

Referring now to FIG. 6, a side view of intra-nasal clip is shown, wherein aromatherapy spheres 601 are placed into distal ends 603. In order to secure placement of aromatherapy spheres 601 in distal ends 603, end-lids 605 must be closed towards distal ends 603. Once end-lids 605 are closed towards distal ends 603, snaps 607 will lock into end-lids 605 to secure aromatherapy spheres 601 inside distal ends 603.

Figure 7:
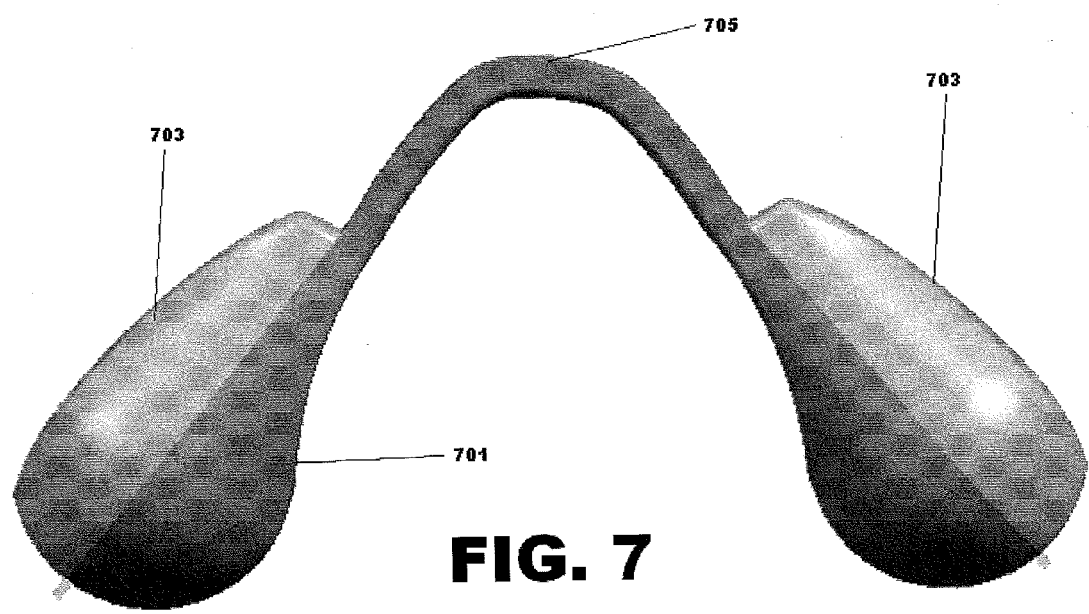
FIG. 7 is a side view of a preferred embodiment of the current invention, intra-nasal dispenser clip.

Referring now to FIG. 7, a side view of intra-nasal clip is shown, wherein end-lids 703 are closed in on distal ends 701. Distal ends 701 are connected with bridge 705.

Figure 8:
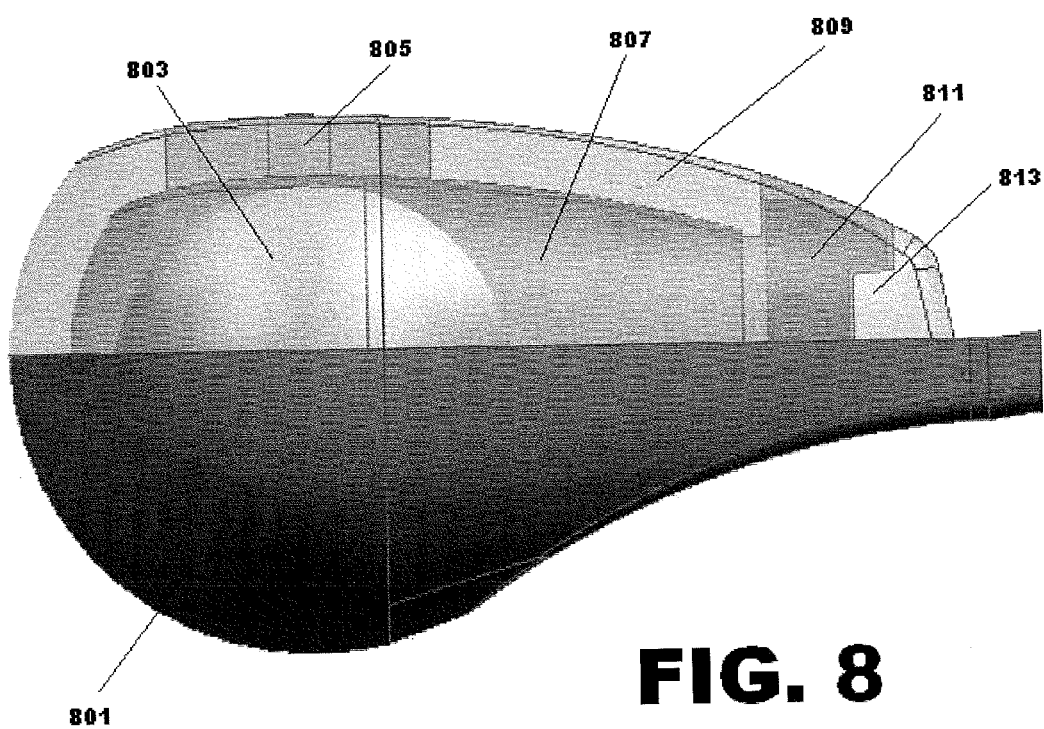
FIG. 8 is a side view of the hollow distal ends orbs containing the aromatherapy spheres.

Referring now to FIG. 8, a side view of distal end of intra-nasal clip is shown, wherein distal ends 801 holds aromatherapy spheres 803. Distal ends 801 is held onto end-lids 809 by snaps 811, which hold end-lids 809 in place to allow distal ends 801 to hold aromatherapy spheres 803. Snaps 811 are held firm by pressure from edge 813 of end-lids 809. End-lids 809 further comprises inlets 805, which may comprise a variety of geometries as best seen fit to allow aromatherapy vapors to be allowed to escape from aromatherapy spheres 803. Hollows 807 are the space between distal ends 801 and end-lids 809 and may contain essential oils, aromatherapy liquids or other substances to best adjust to the need or particular aromatherapy regime.

Figure 9:
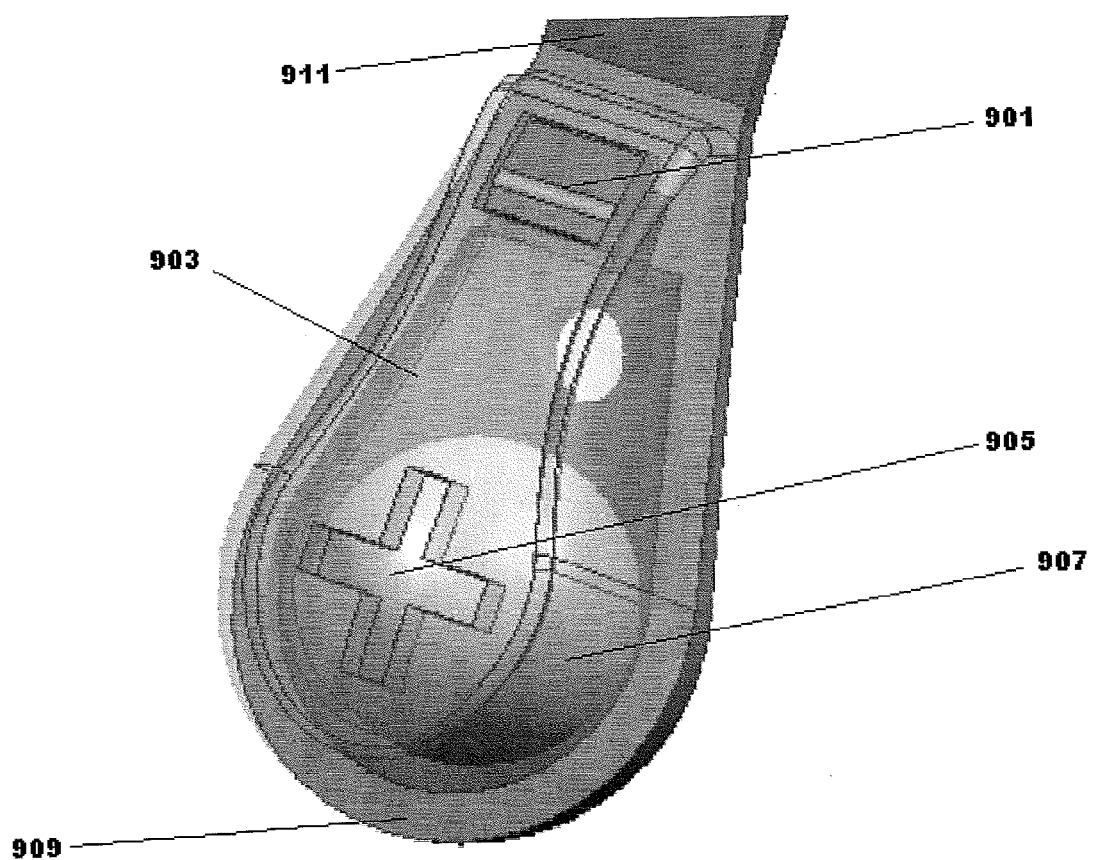
FIG. 9 is a perspective view of the hollow distal ends orbs containing the aromatherapy spheres.

Referring now to FIG. 9, a perspective view of distal end of intra-nasal clip is shown, wherein distal ends 909 which is at the end of bridge 911 holds aromatherapy spheres 907. Distal ends 909 is held onto end-lids 903 by snaps 901, which hold end-lids 903 in place to allow distal ends 909 to hold aromatherapy spheres 907. End-lids 903 further comprises inlets 905, which may comprise a variety of geometries as best seen fit to allow aromatherapy vapors to be allowed to escape from aromatherapy spheres 907.

While the present invention has been described with reference to particular embodiments, it will be understood that the embodiments are merely illustrative and that the invention scope is not so limited. Any variations, modifications, additions, and improvements to the embodiments described are possible. These variations, modifications, additions, and improvements may fall within the scope of the inventions as detailed within the following claims.

What is claimed is:

1. An intra-nasal clip comprising a bridge, a distal end further comprising a bridge end connected to the bridge and an opposite end, opposite the bridge end, wherein a hinge is located at the opposite end and a snap is located at the bridge end of the distal end, an end lid connected to the hinge located at the opposite end and releasably connected to the snap, a second distal end further comprising a second bridge end connected to the bridge and a second opposite end, opposite the second bridge end, wherein a second hinge is located at the second opposite end and a second snap is located at the second bridge end of the second distal end, a second end lid connected to the second hinge located at the second opposite end and releasably connected to the second snap, an aromatherapy sphere for both the distal end and the second distal end, and a plurality of inlets located on both the distal end and the second distal end.

2. The intra-nasal clip of claim 1 wherein the distal end further comprises a hollow which is configured to be filled with the aromatherapy sphere in addition to essential oils, aromatherapy liquids or other substances.

3. The intra-nasal clip of claim 1 wherein the plurality of inlets located on both the distal end and the second distal end further comprises a cross-shaped inlet.

4. The intra-nasal clip of claim 1 wherein the plurality of inlets located on both the distal end and the second distal end further comprises a row of inlets.

5. The intra-nasal clip of claim 1 wherein the distal end further comprises a distal bowl that holds the aromatherapy sphere.

6. The intra-nasal clip of claim 1 wherein the second distal end further comprises a distal bowl that holds the aromatherapy sphere.

* * * * *